United States Patent [19]

Israel

[11] Patent Number: 5,516,654
[45] Date of Patent: *May 14, 1996

[54] PRODUCTION OF RECOMBINANT BONE-INDUCING PROTEINS

[75] Inventor: David I. Israel, Concord, Mass.

[73] Assignee: Genetics Institute, Inc., Cambridge, Mass.

[*] Notice: The term of this patent shall not extend beyond the expiration date of Pat. No. 5,318,898.

[21] Appl. No.: 187,921

[22] Filed: Jan. 27, 1994

Related U.S. Application Data

[63] Continuation-in-part of Ser. No. 679,451, Apr. 2, 1991, Pat. No. 5,318,898.
[51] Int. Cl.⁶ .......................... C12P 21/00; C12P 21/02; C12N 5/02; C12N 5/10
[52] U.S. Cl. .................. 435/69.1; 435/70.3; 435/240.2; 435/240.3
[58] Field of Search .................. 435/69.1, 70.3, 435/240.2, 240.3, 240.25

[56] References Cited

U.S. PATENT DOCUMENTS

| | | | |
|---|---|---|---|
| 3,407,076 | 10/1968 | Ganz | 530/360 |
| 4,994,387 | 2/1991 | Levine et al. | 435/240.2 |
| 5,024,947 | 6/1991 | Inlow et al. | 435/240.31 |
| 5,141,905 | 8/1992 | Rosen et al. | 435/69.1 |

FOREIGN PATENT DOCUMENTS

WO/9217584  10/1992  WIPO.

OTHER PUBLICATIONS

Matsuoka, et al., Tohoku J. Exp. Medicine 149:61–66 (1986).
Israel, et al., Growth Factors 7:139–150 (1992).
Wozney, et al., Science 242:1528–1534 (1988).
Wang, et al., Proc. Nat'l Acad. Sci U.S.A. 87:22202–2224 (1990).
Budavari, et al., "The Merck Index," An Encyclopedia of Chemical Drugs, and Biologicals, 11th Ed., Merck & Co., Inc. (1989).
Papkoff, et al., Mol. and Cell. Biol. 9(8):3377–3384 (1989).
Baba, et al., Proc. Nat'l Acad. Sci. U.S.A. 85:6132–6136 (1988).
Sugawara, et al., Experientia 45:996–998 (1989).
Hammonds, et al., Molecular Endocrinology 5(1);149–155 (1991).

*Primary Examiner*—Marianne P. Allen
*Attorney, Agent, or Firm*—Steven R. Lazar; Thomas J. DesRosier

[57] ABSTRACT

A process for increasing the yield of recombinant bone-inducing proteins of the BMP-2 family is provided, wherein dextran sulfate is added to the culture medium in which cells expressing the proteins are grown.

1 Claim, No Drawings

PRODUCTION OF RECOMBINANT BONE-INDUCING PROTEINS

This application Ser. No. 679,451, filed Apr. 2, 1991, now U.S. Pat. No. 5,318,898. This invention relates to a method for increasing the yield of recombinant bone-inducing proteins of the BMP-2 family.

BACKGROUND OF THE INVENTION

The cloning and expression of the recombinant osteogenic proteins of the BMP-2 family has previously been described (J. M. Wozney, et al., Science 242:1528-1534 (1988); E. A. Wang, et al., Proc. Natl. Acad. Sci. USA 87:2220-2224 (1990), incorporated herein by reference). Osteogenic proteins of the BMP-2 family are a promising development in the bone and cartilage field. The BMP-2 family of proteins includes BMP-3, BMP-4, BMP-5, BMP-6 and BMP-7, and bone-inducing proteins and proteins which are encoded by DNA sequences which hybridize thereto under stringent conditions.

The BMP proteins include BMP-1, BMP-2, BMP-3, BMP-4, BMP-5, BMP-6 and BMP-7, disclosed for instance in United States Patents 5,108,922; 5,013,649; 5,116,738; 5,106,748; 5,187,076; and 5,141,905; BMP-8, disclosed in PCT publication WO91/18098; BMP-9, disclosed in PCT publication WO93/00432; and BMP-10, disclosed in co-pending patent application, serial number 08/061,695, filed on May 12, 1993, now abandoned. They may also include other proteins of the TGF-β superfamily of proteins, such as activins. Examples of activin proteins which may be used in accordance with the methods of the present invention is described in co-pending patent application 08/061,464, filed on May 12, 1993, now abandoned. Examples of members of the TGF-β superfamily of proteins which may be used in accordance with the present invention are Vi-1 and VL-1, which are described in copending patent application 08/164,103, filed on Dec. 7, 1993, now abandoned. The methods of the present invention are also useful with heterodimers of the above BMP proteins and TGF-β proteins. Examples of preparation of such heterodimers are described in copending patent application Ser. No. 07/989,847, filed on Nov. 27, 1992. The disclosures of all of the above references are incorporated herein by reference.

These osteogenic proteins may be produced in cultured mammalian cell lines by transformation with an expression vector containing the respective cDNAs. The yield of expressed recombinant bone-inducing proteins can be increased in accordance with the present invention by addition of dextran sulfate to the cell culture medium.

DESCRIPTION OF THE INVENTION

Genes encoding the foregoing recombinant osteogenic proteins may be expressed in mammalian cell lines such as CHO (Chinese Hamster Ovary), COS, BHK, Balb/c 3T3, 293, and similar cell lines known in the art. The mammalian cells may be grown in any suitable medium, such as e-MEM, Dulbecco's MEM, RPMI 1640, and other media (Freshney, R. I., *Culture of Animal Cells, A Manual of Basic Technique*, Alan R. Liss, Inc., New York (1983)). The cells may be grown in the presence or absence of a serum supplement such as fetal bovine serum (FBS). The cells may be grown in monolayer or suspension culture, and additionally may be grown in large production scale batches. The expressed osteogenic proteins are recovered from the culture medium and can be purified using known methods.

Transformed CHO cells are the preferred host cells used to produce an osteogenic protein of the BMP-2 family in accordance with the present invention. The cell growth medium may be supplemented with FBS to improve the growth of transformed CHO cells in culture. If it is desired to add FBS, concentrations of FBS as low as 0.5% (v/v) may be added. However, addition of animal-origin proteins always presents the risk of harboring viruses and other deleterious agents. The addition of FBS is not necessary for the practice of the present invention.

Any dextran sulfate may be used. One example is dextran sulfate of molecular weight 500,000 and sulfur content 17% (Pharmacia). Another example is dextran sulfate of molecular weight 5,000 and sulfur content 18% (Sigma catalogue # D-7037).

In accordance with the present invention, the growth medium is supplemented with dextran sulfate at a range of concentrations from about 1 to about 500 µg/mL. Higher concentrations of dextran sulfate work but may interfere with cell growth or protein purification. Preferably, the growth medium is supplemented with about 5 µg/ml to about 50 µg/ml dextran sulfate. Most preferably, the growth medium is supplemented with about 10 to 20 µg/ml dextran sulfate.

Expression of BMP-2 can be achieved by inserting a BMP-2 gene into an expression vector, inserting this vector into a mammalian cell, and selecting for cells which express BMP-2. See allowed commonly assigned, patent application Ser. No. 179,100, filed Apr. 8, 1988, now U.S. Pat. No. 5,013,649, the contents of which are incorporated herein by reference.

The yield of recombinant BMP-2 protein from mammalian cells which express the BMP-2 gene may be measured by known methods such as radioactively labeling cells with [$^{35}$S]- methionine and analyzing secreted proteins by polyacrylamide gel electrophoresis (PAGE) and autoradiography. For measurement of BMP-2 expression from production-scale batches, the amount of functional BMP-2 secreted is preferably quantitated by bioassay. Any appropriate bioassay may be used, for example, assay of induction of alkaline phosphatase activity in a BMP-2-responsive cell line, or assay of ectopic bone formation in a mammal such as rat, rabbit, cat or dog.

The optimal concentration of dextran sulfate for increasing yield of BMP-2 was determined by pulse labelling cells with [$^{35}$S]-methionine, followed by a four hour chase in varying amounts of dextran sulfate. Total secreted protein was then analyzed by PAGE and autoradiography. Cells were analyzed under two growth conditions: 1) standard adherent monolayers, and 2) suspension and serum free adapted cultures. Two different sizes of dextran sulfate (5000 dalton and 500,000 dalton) were tested for each growth condition. A concentration range of 1 µg/ml to 1000 µg/ml was examined for each size dextran sulfate on each growth state.

The results demonstrate that the potency of the 5000 dalton material was similar to the 500,000 dalton dextran sulfate for both monolayer and suspension cells. For cells grown in suspension, 1 µg/ml dextran sulfate produced a small increase in BMP-2 levels. Yield was near maximal at 10 µg/ml, and was approximately three-fold higher than in the absence of dextran sulfate. Increasing the dextran sulfate concentration to 100 µg/ml elicited a further 10% increase in BMP-2 yield. As another example, BMP-2 yield was about 40% higher utilizing 1000 µg/ml dextran sulfate than utilizing 10 µg/ml dextran sulfate. In other words 1000 µg/ml dextran sulfate yielded approximately four-fold more BMP-2 than was obtained in the absence of the compound.

While a similar graded response was observed with monolayer cells, the potency of dextran sulfate in increasing BMP-2 yield was reduced about 10-fold. Threshold effects were seen at 10 µg/ml, while levels of 100–300 µg/ml were needed to elicit a near-maximal response. Typically, 100 µg/ml dextran sulfate was used to increase the yield of BMP-2 from cells grown in monolayers. The magnitude of the dextran sulfate effect was about four-fold, similar to that seen with suspension cells.

The yield of the other osteogenic proteins, BMP-3, BMP-4, BMP-5, BMP-6 and BMP-7, may similarly be improved with the addition of dextran sulfate to the cell culture medium.

What is claimed is:

1. In a process for producing a recombinant bone-inducing protein of the BMP-2 family which comprises culturing in a suitable culture medium a mammalian host cell grown in suspension, said host cell being transformed with a gene encoding BMP-7, and recovering the protein from said culture medium, the improvement for increasing the yield of said bone-inducing protein which comprises adding about 1 to about 1,000 µg/ml dextran sulfate to said culture medium.

* * * * *